United States Patent [19]

Walsh

[11] Patent Number: 5,316,764
[45] Date of Patent: * May 31, 1994

[54] CANINE PARVOVIRUS VACCINES

[75] Inventor: Jill Walsh, Houghton, England

[73] Assignee: AKZO N.V., Arnhem, Netherlands

[*] Notice: The portion of the term of this patent subsequent to Mar. 7, 2006 has been disclaimed.

[21] Appl. No.: 25,713

[22] Filed: Feb. 25, 1993

Related U.S. Application Data

[63] Continuation of Ser. No. 319,804, Mar. 6, 1989, abandoned, which is a continuation of Ser. No. 823,333, Jan. 28, 1986, Pat. No. 4,810,494.

[30] Foreign Application Priority Data

Jan. 30, 1985 [GB] United Kingdom ............... 8502399

[51] Int. Cl.$^5$ ............... A61K 39/12; A61K 39/23
[52] U.S. Cl. ............... 424/89; 424/93 R; 424/93 T; 435/235.1; 435/236; 435/237; 435/238
[58] Field of Search ............... 435/235.1, 236, 237, 435/238; 424/89, 93 R, 93 T

[56] References Cited

U.S. PATENT DOCUMENTS 4,303,645 12/1981 Carmichael et al. ............... 424/89
4,810,494 3/1989 Welsh ............... 424/89

OTHER PUBLICATIONS

Wilson et al., Vet Q., 4(3): 108-116 (1982).
O'Brien et al., J. Am. Vet. Med. Assoc., 188(7): 699-701 (1986).
"A Research Update: Canine Parvovirus", Ralston-Purina Co. (1980).
Appel, "Canine Parvovirus Infection" Cornell Research Laboratory for Diseases of Dogs, Laboratory Report, Series 3, No. 1 (Mar. 1979).

*Primary Examiner*—Toni R. Scheiner
*Attorney, Agent, or Firm*—John W. Schneller; William M. Blackstone

[57] ABSTRACT

The present invention concerns a vaccine comprising a novel canine parvovirus strain and having the property of being able to break through the maternally derived antibody levels persistent in 9-12 week old pups, and even to immunize the majority of pups at the age of 6 weeks in the presence of maternally derived antibodies.

16 Claims, No Drawings

CANINE PARVOVIRUS VACCINES

This application is a continuation of application Ser. No. 07/319,804, filed Mar. 6th, 1989, now abandoned, which is a continuation of application Ser. No. 06/823,333, filed Jan. 28th, 1986 now U.S. Pat. No. 4,810,494.

The present invention involves a novel canine parvovirus vaccine, a method for the production thereof, a novel canine parvovirus strain, and a method for the protection of dogs against canine parvovirus infection.

An infection of dogs and especially of young dogs with canine parvovirus (CPV) frequently leads to an enteric disease characterized by acute diarrhea, fever and leukopenia (relative lymphophenia).

Vaccines have been developed to prevent infection of dogs with CPV. These vaccines, however, are often not effective when given in the presence of maternally derived antibody (MDA). In certain puppies this passive immunity may persist for a considerable period (4 months or more) at levels sufficient to interfere with vaccination. Latterly, as the MDA level declines a pup may be protected insufficiently against infection and disease, but still be refractory to vaccination. Hence these puppies remain unprotected during a considerable period in their early life; particularly after the maternally derived immunity has vanished the danger of infection of complete litters poses a serious risk.

For this reason there is a need for a CPV vaccine which will successfully immunize puppies earlier in their lifes.

The aim of the present invention is to furnish such a vaccine.

The vaccine according to the invention is characterized in that it comprises viruses derived from a CPV strain with the internal notation 154. Samples of this virus strain have been deposited at the Collection Nationale de Cultures de Microorganismes of the Institut Pasteur at Paris, France, under no. I-404.

Vaccines according to the invention preferably comprise the CPV strain in the live attenuated form.

Attenuation is established by serial passages of the viruses in a culture of cells originating from a canine or feline species at a temperature of about 37° C. For each step the viruses harvested from the previous culture step are inoculated to a medium containing a fresh cell culture. For the culturing of the cells use is made of methods known in the art.

For the preparation of the vaccine the thus attenuated seed virus can be grown on a cell culture, such as a feline embryo fibroblast (FEF) culture. Preferably this is done at a temperature which is normal for the dog. The viruses thus grown can be harvested by collecting the tissue cell culture fluids and/or cells. Optionally, during the harvesting the yield of the viruses can be promoted by techniques which improve the liberation of the infective particles from the growth substrate, e.g. sonication. The vaccine may be prepared in the form of a suspension or may be lyophilized. In lyophilized CPV vaccines it is preferable to add one or more stabilizers. Suitable stabilizers are for example SPGA (described by Bovarnick (1950) J. Bacteriology 59, 509), carbohydrates (such as sorbitol, mannitol, starch, sucrose, dextran, glucose), proteins (such as albumin or casein) or degradation products thereof, protein containing agents (such as bovine serum or skimmed milk) and buffers (such as alkali metal phosphates). Optionally, one or more compounds having adjuvant activity may be added too. Suitable adjuvants are for example aluminum hydroxide, phosphate or oxide, mineral oils (such as Bayol F ®, Marcol 52 ®) and saponins.

Vaccines according to the invention alternatively may comprise the CPV strain in inactivated form.

Inactivated CPV vaccines according to the invention are prepared from viruses from which both replication and virulence have been abolished. In general this can be attained by chemical or by physical means. Chemical inactivation can be carried out by treatment of the viruses for example with enzymes, with formaldehyde, β-propiolacton or ethyleneimine or a derivative thereof, with an organic solvent (such as a halogenated hydrocarbon) and/or with a detergent (such as Tween ®, Triton X ®, sodiumdesoxycholate, sulfobetain or cetyltrimethylammonium salts). Physical inactivation advantageously can be carried out by subjecting the viruses to energy-rich radiation, such as UV light, γ-radiations or X-rays. If necessary the inactivating agent is neutralized; for example formaldehyde-inactivated preparations can be neutralized with thiosulphate. If required, the pH subsequently is returned to a value of about 7. Generally, also an adjuvant is added to the inactivated viruses, and optionally one or more emulsifiers, such as Tween ® and Span ®.

The virus strain 154 was identified as a canine parvovirus by the following characteristics:

(i) Its ability to grow in feline and canine cells.
(ii) Its failure to grow in both feline and canine cells that were not dividing.
(iii) The production of haemagglutinins in cell culture that would agglutinate porcine erythrocytes at pH 7.2, but not those of humans or rodents.
(iv) The production of typical nuclear inclusions in cell culture.
(v) Its neutralization by feline and rabbit antiserum prepared against feline panleucopenia virus and known canine parvovirus.
(vi) The inhibition of haemagglutination by antiserum prepared against feline panleucopoenia virus and known canine parvovirus.

The novel CPV strain furthermore is distinguished from the hitherto known CPV strains by the following set of properties:

a. Its ability to grow well in fibroblastic type cells of both feline and canine origin at a temperature of 37° C. with the production of characteristic cytopathic effect. In comparison with known CPV strains the strain according to the invention shows growth characteristics as summarized in Table I:

TABLE I

Ability of different CPV strains to grow on different cell culture systems.

| Cell culture meeting CPV strain | A 72 | FEF | CRFK |
|---|---|---|---|
| Boostervac ® (C-vet) | − | + + + + | + + + |
| Enduracell ® (Smith-Kline) | + | − | + |
| Nobivac P.C. (novel vaccine according to invention) | + + + + | + + | + + + |

TABLE I-continued

Ability of different CPV strains to grow on different cell culture systems.

| Cell culture meeting | A 72 | FEF | CRFK |
|---|---|---|---|
| Wild type | +++ | +++ | +++ |

Legends:
A 72 = Binn's canine fibroblastic cell-line
FEF = Feline embryo fibroblastic cell-line
CRFK = Crandall feline kidney cell-line
++++ = widespread cytopathic effect (CPE) and haemagglutination (HA) at first passage
+++ = slight CPE at first passage
++ = CPE and HA at point of second passage
+ = CPE developing after second passage
− = no CPE and HA after repeated passages.

b. The production of large, distinct plaques under agar in the aforementioned cell lines.

From these data it can be concluded that the CPV strain 154 represents a novel virus strain.

The virus strain 154 was obtained from the feces of a puppy showing the symptoms of a CPV infection. However, it may also be isolated from intestinal tract samples, thymus or other lymphoid tissues, bone marrow, blood or liver from puppies or dogs infected with the virus. The sample material may be purified and diluted with buffered saline or cell culture medium prior to inoculation onto actively dividing cells of canine or feline origin.

In contrast to the vaccines comprising known virus strains, the vaccine according to the invention is effective in the majority of puppies at 6 weeks of age and in virtually 100% of puppies at 9–12 weeks of age. This means that the novel CPV viruses are able to break through the eventually present maternally derived antibodies persistent at that age without, however, causing symptoms of a CPV infection in the vaccinated puppies.

Maternal antibody titers at 12 weeks have usually declined below 1:32 and levels in excess of 1:32 are very rare at 12 weeks. Close to 100% of the animals with a titre of 1:32 will respond to vaccination with the vaccine according to the invention, and even at a level of 1:64 the majority of the pups will respond.

Suitable vaccination schemes for pups known or suspected to possess maternal antibodies against CPV are for example either a single vaccination at the age of 12 weeks, or repeated vaccinations starting from the age of 6 weeks (e.g. at 6, 9 and 12 weeks), or weekly vaccinations from 4 weeks on.

If no information as to the presence of maternal antibodies is available it is generally recommended to vaccinate at the age of 12 weeks.

The recommended dose for the live attenuated vaccine is up from $10^3$ $TCID_{50}$, however, in puppies having MDA's preferable at least $10^6$ $TCID_{50}$ per puppy.

Administration of these vaccines can be done parenterally (e.i. injection) or enterally (e.i. by oral administration).

Also part of the invention are combination vaccines which apart from the CPV vaccine virus described above comprise at least one of the following canine vaccine viruses: canine distemper, infectious canine hepatitis (CAV-1 and CAV-2), rabies, parainfluenza, canine corona virus, measles, and/or the infectious bacteria leptospirosis and Bordetella.

In order to test the pathogenicity, immunogenicity and enhancement of virulence during transmission the CPV was serially transmitted to 7 subsequent dogs. In this study 18 pups were used, which all were antibody free at the time of exposure. All pups remained well throughout the observation periods, and demonstrated antibody responses. White cell counts remained within the normal range.

The efficacy of the protection by vaccination with the vaccine according to the invention was shown by exposing 4 puppies which had shown antibody response to 6 week vaccination together with two unvaccinated controls to a virulent CPV strain. The unvaccinated dogs developed clinical signs characteristic of CPV infection, whereas the vaccinated puppies did not.

EXAMPLE 1

Isolation and passaging of virus

The virus was isolated from a rectal swab taken from a clinical case of parvovirus infection that occurred in an eight week old beagle puppy in a breeding kennel.

The virus was inoculated to a culture of FEFs and passaged a further time in these cells before transfer to cultures of the canine A72 cell line. [Binn, Marchwicki & Stephenson A.M.J.V.R. v. 41 p. 855–860 (1981)]. All passages of virus in cell culture were performed at 37° C.

The virus was subsequently attenuated through 41 passages in this cell line, in the course of which 4 cloning steps were made at 4th, 7th, 10th and 40th passage levels. On each occasion, a large clear isolated plaque was picked.

Virus of 41st passage in A72 cells (POOL 182) was then inoculated back into FEF cultures and the harvest of the 2nd passage in FEFs beyond POOL 182 was layed down as a "MASTER SEED" LOT and designated POOL 190.

EXAMPLE 2

Preparation of live vaccine

A. Primary and secondary working seed lots are prepared from the master seed lot obtained according to Example 1. These are four and five FEF cell culture passages beyond the transition from the A72 cell line. FEF cell cultures are infected as seeding with the working seed virus. The cultures are then incubated until the viral cytopathic effects have reached the appropriate stage. At this time the cell culture medium is harvested and stored at −70° C.

B. Samples of the harvest are assayed for virus titer and tested for sterility. When the virus titer is known, the virus is blended with stabiliser to give 5.5% sorbitol and 5.5N % amine (a pancreatic digest of casein) in the finished blend. The blend is then filled out into neutral glass vials in 1.0 ml volumes, and subsequently freeze-dried and sealed under vacuum.

EXAMPLE 3

Vaccination of pups taking into respect maternal antibodies

A vaccine containing a CPV dose of $10^{7.4}$ $TCID_{50}$ was administered to 135 pups containing varying levels of maternally derived antibody (MDA) titers established by hemagglutination inhibition. 124 of these were vaccinated at the age of 6 weeks, the remaining 11 were vaccinated at the age of 9 weeks. A minor part of the pups did not serologically respond to the vaccination at week 6; these were revaccinated at 8–9 weeks of age, and in all cases they responded with a prompt seroconversion.

A summary of the results is given in Tables 2 and 3:

TABLE 2
Serological response of puppies after one vaccination.

| MDA titers at 6 weeks | No. of pups | Percentage of total pups studied (%) | Number vaccinated at 6 weeks | serological response following vaccination at 6 weeks | | Number vaccinated at 9 weeks | serological response following vaccination at 9 weeks | |
|---|---|---|---|---|---|---|---|---|
| | | | | number | % | | number | % |
| <20 | 16 | 12 | 12 | 10 | 83 | 4 | 4 | 100 |
| 20 | 18 | 13 | 16 | 15 | 94 | 2 | 2 | 100 |
| 40 | 51 | 38 | 50 | 44 | 88 | 1 | 1 | 100 |
| 80 | 39 | 29 | 37 | 26 | 70 | 2 | 2 | 100 |
| 160 | 11 | 8 | 9 | 7 | 78 | 2 | 2 | 100 |
| | 135 | | 124 | 102 | 82 (mean) | 11 | 11 | 100 (mean) |

TABLE 3
Serological response of puppies non responding upon vaccination at 6 weeks and revaccinated at 8-9 weeks

| MDA titers at 6 weeks | Number re-vaccinated at 8-9 weeks | Serological response | |
|---|---|---|---|
| | | number | % |
| <20 | 2 | 2 | 100 |
| 20 | 1 | 1 | 100 |
| 40 | 6 | 6 | 100 |
| 80 | 11 | 11 | 100 |
| 160 | 2 | 2 | 100 |
| | 22 | 22 | 100 |

EXAMPLE 4
Comparison of efficacy of the vaccine with others in the presence of detectable maternally derived antibodies The efficacies of three different vaccines were compared in two separate trials.

In the first trial the young born in a beagle colony were vaccinated with either the Smith-Klines live attenuated CPV vaccine (SK-CPV) or the Intervet Feline Parvovirus vaccine (FPV).

In the second trial puppies born in a beagle colony were vaccinated with either a live CPV-vaccine according to the invention (Int-CPV) or the Intervet Feline Parvovirus vaccine (FPV).

The pups were vaccinated weekly from 4-8 weeks of age. All pups had received maternal antibodies from their damns.

The results are shown in Table 4.

TABLE 4

| | first trial | | second trial | |
|---|---|---|---|---|
| | SK-CPV | FPV | Int-CPV | FPV |
| numbers of litters treated | 27 | 38 | 16 | 16 |
| number of young born alive | 156 | 212 | 108 | 91 |
| number of young weaned and vaccinated | 136 | 194 | 99 | 84 |
| number of deaths postweaning due to CPV infeciton | 15 | 21 | 4 | 11 |
| % deaths due to CPV infection | 11.0 | 10.8 | 4 | 13.1 |
| number of sick puppies, recovered after treatment | 24 | 35 | 2 | 18 |
| total % showing clinical CPV disease | 28.7 | 28.9 | 6 | 34.5 |

The conclusion can be drawn that immunization of puppies with the vaccine according to the invention results in a protection against fatal CPV disease which is by far superior to the protection gained by the known vaccines.

EXAMPLE 5
Preparation of inactivated vaccine

The cell culture medium obtained according to Example 2 (having a titre of 10/8 tcid/50 per ml) is treated with $\beta$-propiolactone at a concentration of 0.1% during a 2 hours incubation at 37° C.

The bulk fluid is neutralized at intervals by the dropwise addition of 1N NaOH. Phenol red (present in the culture medium) gives an indication of when pH adjustment is necessary.

Finally aluminium phosphate is blended with the mixture to a final concentration of 0.3% as adjuvant.

EXAMPLE 6
Response of maternally immune pups to vaccination at the age of 12 weeks Two groups of pups showing considerable titers of maternal antibodies were immunised with either the live vaccine prepared according to Example 2, or with the heterotypic, feline parvovirus based vaccine.

The maternal antibodies were determined by hemagglutination inhibition titration.

In each group three different dose regimes were applied, and each group comprised 9 pups.

The results are given in Table 5.

TABLE 5

| dose/pup (in tcid/50) | dog no. | MDA at vaccination (HI titre) | response |
|---|---|---|---|
| GROUP I: Nobivac PC | | | |
| 10/6 | 1 | 16 | no |
| | 2 | 32 | no |
| | 3 | 16 | yes |
| 10/7 | 4 | 16 | yes |
| | 5 | 8 | yes |
| | 6 | 32 | yes |
| 10/8 | 7 | 16 | yes |
| | 8 | 32 | yes |
| | 9 | 32 | yes |
| GROUP II: Feline parvovirus vaccine | | | |
| 10/6 | 10 | 16 | no |
| | 11 | 16 | no |
| | 12 | 8 | no |
| 10/7 | 13 | 16 | no |
| | 14 | 8 | no |
| | 15 | 16 | no |
| 10/8 | 16 | 8 | no |
| | 17 | 4 | yes |
| | 18 | 8 | no |

I claim:

1. A vaccine for immunization against canine parvovirus infections comprising an immunologically effective amount of canine parvovirus derived from strain 154, CNCM number I-404 and having the immunogenic characteristic of eliciting an antibody response in pups having maternally derived antibodies against canine parvovirus, and a pharmaceutically acceptable carrier.

2. The vaccine of claim 1, wherein the canine parvovirus is obtained by passaging strain 154, CNCM number I-404.

3. The vaccine according to claim 1, wherein said canine parvovirus is in attenuated live form.

4. The vaccine according to claim 1, wherein said canine parvovirus is inactivated.

5. The vaccine of claim 1, wherein said parvovirus is prepared by passage through a feline or canine cell line.

6. A biologically pure culture of canine parvovirus derived from strain 154, CNCM number I-404, and having the immunogenic characteristic of eliciting an antibody response in pups having maternally derived antibodies against canine parvovirus.

7. The canine parvovirus of claim 6, prepared by passaging strain 154, CNCM number I-404.

8. The culture according to claim 6, wherein said canine parvovirus is in attenuated live form.

9. The culture according to claim 6, wherein said canine parvovirus is inactivated.

10. The culture of claim 6, wherein said canine parvovirus is prepared by passage through a feline or canine cell line.

11. The culture of claim 10, wherein said canine parvovirus is prepared by passage through a feline embryo fibroblast cell line.

12. A combination vaccine for the immunization of canines comprising canine parvovirus derived from strain 154, CNCM number I-404, and having the immunogenic characteristic of eliciting an antibody response in pups having maternally derived antibodies against canine parvovirus, and at least one other canine vaccine, both in an immunologically effective amount, and a pharmaceutically acceptable carrier.

13. The combination vaccine of claim 12, wherein said other canine vaccine is selected from the group consisting of canine distemper virus, infectious canine hepatitis virus CAV-1, infectious canine hepatitis virus CAV-2, rabies, para influenza, canine corona, and measles virus vaccines.

14. The combination vaccine of claim 13, wherein said other canine vaccine additionally comprises an immunologically effective amount of a bacterial vaccine selected from the group consisting of leptospirosis and Bordetella vaccines.

15. The combination vaccine according to claim 12, wherein said other canine vaccine is an immunologically effective amount of a bacterial vaccine selected from the group consisting of leptospirosis and Bordetella vaccines.

16. The vaccine of claim 5, wherein said parvovirus is prepared by passage through a feline embryo fibroblast cell line.

* * * * *

UNITED STATES PATENT AND TRADEMARK OFFICE
CERTIFICATE OF CORRECTION

PATENT NO. : 5,316,764
DATED : May 31, 1994
INVENTOR(S) : Jill Welsh

It is certified that error appears in the above-identified patent and that said Letters Patent is hereby corrected as shown below:

On the title page, Item [19] and [75];
    correct the inventor's name on the title page by deleting "Walsh"

-- Welsh --.

Signed and Sealed this

Thirteenth Day of September, 1994

Attest:

BRUCE LEHMAN

*Attesting Officer*     *Commissioner of Patents and Trademarks*